(12) United States Patent
Danilkin et al.

(10) Patent No.: US 11,992,347 B2
(45) Date of Patent: May 28, 2024

(54) MEDICAL DEVICE CART WITH A TILTED HOLDER

(71) Applicant: Canon U.S.A., Inc., Melville, NY (US)

(72) Inventors: Aleksey Danilkin, Waltham, MA (US); Zachary Hastings, Sterling, MA (US); Jacquelyn Nicole Phelps, Cambridge, MA (US); Jacob Brauer, Cambridge, MA (US); Alexander Altshuler, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 574 days.

(21) Appl. No.: 17/178,076

(22) Filed: Feb. 17, 2021

(65) Prior Publication Data

US 2021/0259796 A1 Aug. 26, 2021

Related U.S. Application Data

(60) Provisional application No. 63/062,245, filed on Aug. 6, 2020, provisional application No. 62/979,953, filed on Feb. 21, 2020.

(51) Int. Cl.
*A61B 50/13* (2016.01)
*A61B 50/20* (2016.01)
(Continued)

(52) U.S. Cl.
CPC ............. *A61B 50/13* (2016.02); *A61B 50/20* (2016.02); *B62B 3/04* (2013.01); *B62B 3/1424* (2013.01);
(Continued)

(58) Field of Classification Search
CPC ......... A61B 50/10; A61B 50/13; A61B 50/15; A61B 50/18; A61B 50/20; A61B 50/22;
(Continued)

(56) References Cited

U.S. PATENT DOCUMENTS 3,116,828 A * 1/1964 Glassman ............... A61B 50/20
D24/229
4,266,669 A * 5/1981 Watson .................... B65D 1/36
D24/227
(Continued)

OTHER PUBLICATIONS

Web, Mammotome revolve ST In-service Quick Guide, Devicor Medical Products, Inc., Mar. 2014, MDM#12-0087, 2 pages, https://www.mammotome.com/wp-content/uploads/2015/10/MDM12-0087-Mammotome-revolve-ST-In-Service-Quick-Guide.pdf.

*Primary Examiner* — Joshua E Rodden
(74) *Attorney, Agent, or Firm* — Canon U.S.A., Inc. IP Division

(57) ABSTRACT

A medical cart apparatus includes at least one component and at least one holster that is tilted with respect to a horizontal plane and is configured to hold or store the at least one component. The medical cart apparatus is ergonomic and conveniently and securely stores elements in the cart. The holster is configured as a storage area, holder, or receptacle, and the holster has a back wall, at least one side, at least one side cut-out, a lip at an entrance of the holster, and a bottom surface that is tilted at the angle with respect to the horizontal plane. The side cut-outs of the holster provide visibility by showing whether a component is in the holster or not, and provide accessibility by facilitating or allowing easy insertion and easy takeout of the at least one component from the holster.

25 Claims, 15 Drawing Sheets

(51) Int. Cl.
    *B62B 3/04*        (2006.01)
    *B62B 3/14*        (2006.01)
(52) U.S. Cl.
    CPC ... *A61B 2560/0493* (2013.01); *B62B 2202/48* (2013.01); *B62B 2202/56* (2013.01)
(58) Field of Classification Search
    CPC ......... A61B 50/24; A61B 50/26; A61B 50/28; A61B 50/33; A61B 2050/105; A61B 2050/155; A61B 2050/185; A61B 2560/0493; B62B 3/04; B62B 3/1424; B62B 2202/48; B62B 2202/56
    USPC .............. 206/363, 438; 211/60.1, 85.13, 124
    See application file for complete search history.

(56)                References Cited

U.S. PATENT DOCUMENTS

| | | | | |
|---|---|---|---|---|
| D277,314 | S | 1/1985 | Alvarez et al. | |
| 4,936,449 | A * | 6/1990 | Conard | A61M 5/3205 |
| | | | | 206/382 |
| 5,000,407 | A * | 3/1991 | Juji | A61M 1/0236 |
| | | | | 280/47.35 |
| 5,615,678 | A * | 4/1997 | Kirkham | A61B 8/44 |
| | | | | 600/459 |
| 6,345,873 | B1 * | 2/2002 | Kim | F16L 3/223 |
| | | | | 248/68.1 |
| 6,447,451 | B1 * | 9/2002 | Wing | G01S 15/899 |
| | | | | 600/437 |
| 6,629,927 | B1 * | 10/2003 | Mesaros | A61B 50/13 |
| | | | | 600/437 |
| 6,980,419 | B2 * | 12/2005 | Smith | G01S 7/52082 |
| | | | | 361/679.41 |
| D675,471 | S | 2/2013 | Averty | |
| 9,033,162 | B2 * | 5/2015 | Brotzman | A61B 50/20 |
| | | | | 211/126.14 |
| D760,529 | S | 7/2016 | Hakansson | |
| D809,664 | S | 2/2018 | Ma et al. | |
| D879,534 | S | 3/2020 | Donaghey | |
| D894,658 | S | 9/2020 | Davenport | |
| D903,872 | S | 12/2020 | Wang | |
| D914,208 | S | 3/2021 | Shabudin et al. | |
| D917,716 | S | 4/2021 | Malvoisin | |
| D930,838 | S | 9/2021 | Meraviglia et al. | |
| D934,445 | S | 10/2021 | Kaplun et al. | |
| 11,382,495 | B2 * | 7/2022 | Awadu | A61B 1/0014 |
| 2002/0092816 | A1 * | 7/2002 | Kim | F16L 3/223 |
| | | | | 248/68.1 |
| 2004/0144673 | A1 * | 7/2004 | Buczek | A61B 50/33 |
| | | | | 206/438 |
| 2004/0186357 | A1 * | 9/2004 | Soderberg | A61B 5/681 |
| | | | | 600/300 |
| 2005/0159784 | A1 * | 7/2005 | Arceta | A61G 12/001 |
| | | | | 607/20 |
| 2009/0166306 | A1 * | 7/2009 | Ahearn | A61G 15/16 |
| | | | | 211/85.13 |
| 2011/0203957 | A1 * | 8/2011 | Zoland | A61B 50/24 |
| | | | | 211/85.13 |
| 2012/0187104 | A1 * | 7/2012 | Heymann | A61B 50/20 |
| | | | | 219/385 |
| 2013/0001180 | A1 * | 1/2013 | Stout | A61B 50/20 |
| | | | | 211/85.13 |
| 2014/0051923 | A1 * | 2/2014 | Mirza | A61B 50/20 |
| | | | | 600/103 |
| 2014/0116647 | A1 * | 5/2014 | Kannry | A61B 50/13 |
| | | | | 165/80.5 |
| 2016/0134107 | A1 * | 5/2016 | Fallat | G02F 1/133308 |
| | | | | 307/20 |
| 2016/0317984 | A1 | 11/2016 | Armstrong et al. | |
| 2018/0185111 | A1 * | 7/2018 | Shuart | A61B 50/20 |
| 2020/0164231 | A1 * | 5/2020 | Cannata | A61N 7/00 |
| 2021/0015456 | A1 * | 1/2021 | Chiang | A61B 8/0883 |
| 2022/0315081 | A1 * | 10/2022 | Stathis | B62B 3/005 |

* cited by examiner

MEDICAL DEVICE CART WITH A TILTED HOLDER

CROSS REFERENCE TO RELATED APPLICATIONS

The present application claims the benefit of priority from U.S. Provisional Patent Application No. 62/979,953 filed Feb. 21, 2020, U.S. Provisional Patent Application No. 63/062,245 filed Aug. 6, 2020, and U.S. Design Application No. 29/747,352 filed Aug. 21, 2020, each of which is hereby incorporated by reference herein in their entirety.

BACKGROUND

Field of the Disclosure

The present disclosure generally relates to medical carts and, more particularly, to a medical cart apparatus with a tilted holder.

Description of the Related Art

Medical carts are used throughout the medical community to functionally implement, assist or accommodate various types of medical procedures, treatment, diagnostics, or the like. Medical carts can conveniently carry or support a variety of medications, medical instruments, tools, supplies, or the like, to accommodate medical personnel or technicians in assisting in the treatment of patients or the like.

A horizontal, exposed holster may cause damage to elements on the cart when the cart is moved or in contact with surroundings. A horizontal or hole-like holster is not ergonomic or easy to place elements in the holster by a user. A hanging holster on the side of the cart may cause a user, wall or other object to hit elements on the cart and cause damage.

It would be beneficial to overcome these concerns and facilitate a medical cart apparatus that is ergonomic and conveniently and securely stores elements in the cart.

SUMMARY

According to an aspect of the present disclosure, a medical cart apparatus includes at least one component and at least one holster that is tilted with respect to a horizontal plane and is configured to hold or store at least one component. The medical cart apparatus is ergonomic and conveniently and securely stores elements in the cart.

According to an additional aspect of the present disclosure, the holster is configured as a storage area, holder, or receptacle, and the holster has a back wall, at least one side, at least one side cut-out, a lip at an entrance of the holster, and a bottom surface that is tilted at the angle with respect to the horizontal plane. The side cut-outs of the holster provide visibility by showing whether a component is in the holster or not, and provide accessibility by facilitating or allowing easy insertion and easy takeout of the at least one component from the holster. Dimensions of the holster are configured to optimize ergonomic access of at least one component contained therein.

According to an additional aspect of the present disclosure, the holster is positioned at an elevation H, wherein a tilt of a bottom surface of the holster is an angle $\theta$ with H being within a range of 55 to 95 cm and $\theta$ being within a range of 5 to 55° to facilitate convenient placement and removal by hand. An upper cover of the apparatus extends horizontally shorter than a base of the holster base by 3 cm or more with a hand clearance of 2 cm or more. The upper cover includes at least one slanting at an edge with an inclination $\theta+\alpha$, where $\alpha$ is up to 45°.

According to an additional aspect of the present disclosure, the medical cart includes one or more of a PIU (patient interface unit), a medical device, a controller, and a display. The medical device can be a catheter. The holster can include circular padding in an area to attach the at least one component, and the holster can include durable coating applied to a surface that holds the PIU. The PIU can include a probe connector and a motor that are controlled by the controller. The PIU can include optical components. The controller performs image processing steps in one or more imaging modes or modalities, and controls information to be displayed on the display. The display can be a touch screen display. The PIU can include at least one functional or voice recognition input. The controller can perform artificial intelligence or machine learning, wherein the artificial intelligence or machine learning is iterative.

According to an additional aspect of the present disclosure, the medical cart apparatus can be a cart that is mobile, portable, or movable to facilitate movement of the cart on a floor or surface. The medical cart apparatus has an upper section and a lower section. The upper section is attached to or integrally formed together with the lower section at an inclined angle. The holster is configured in the upper section. The lower section includes a support hook under the holster. The lower section is mounted on a base that supports the cart with one or more wheels or rollers rotatably attached to the base. The lower section has a base that supports the cart with at least one wheel or roller rotatably attached to the base. The at least one wheel or roller is lockable to lock the apparatus in position.

Further features of the present disclosure will become apparent from the following description of exemplary embodiments with reference to the attached drawings.

DESCRIPTION OF THE EMBODIMENTS

Various exemplary embodiments, features, and aspects of the disclosure will be described with reference to the drawings.

In the following embodiments, medical cart apparatus, device, configurations, or the like, for conveying medical supplies or remote service functions to patients or users or to functionally implement, assist or accommodate various types of medical procedures, treatment, diagnostics, or another use, are described that may have different characteristics, advantages, disadvantages, performance parameters, or the like. The present disclosure is not limited to any particular configuration.

Figure 1:
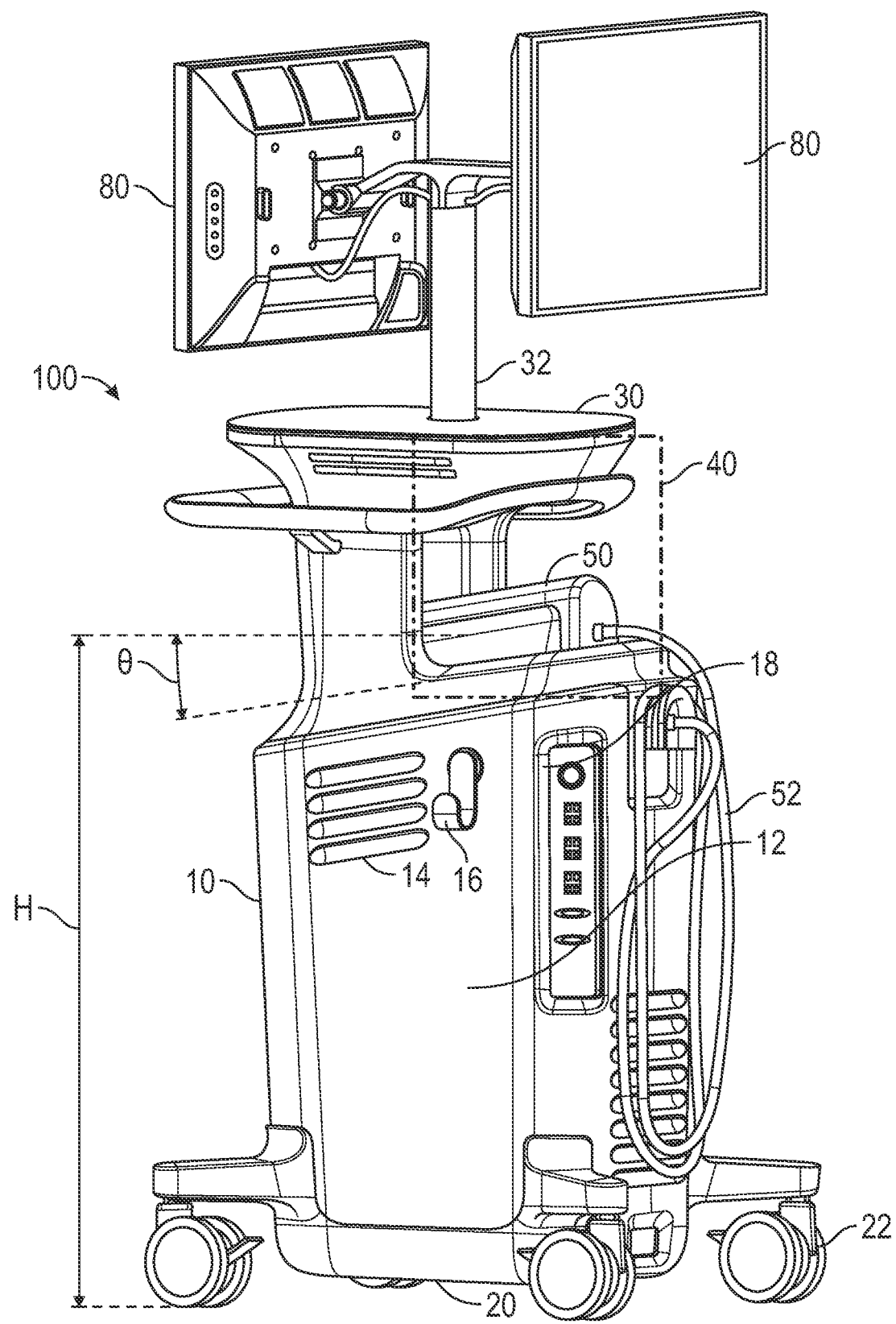
FIGS. 1 and 2 illustrate left side perspective views of a medical cart apparatus according to one or more aspects of the present disclosure.
Figure 2:
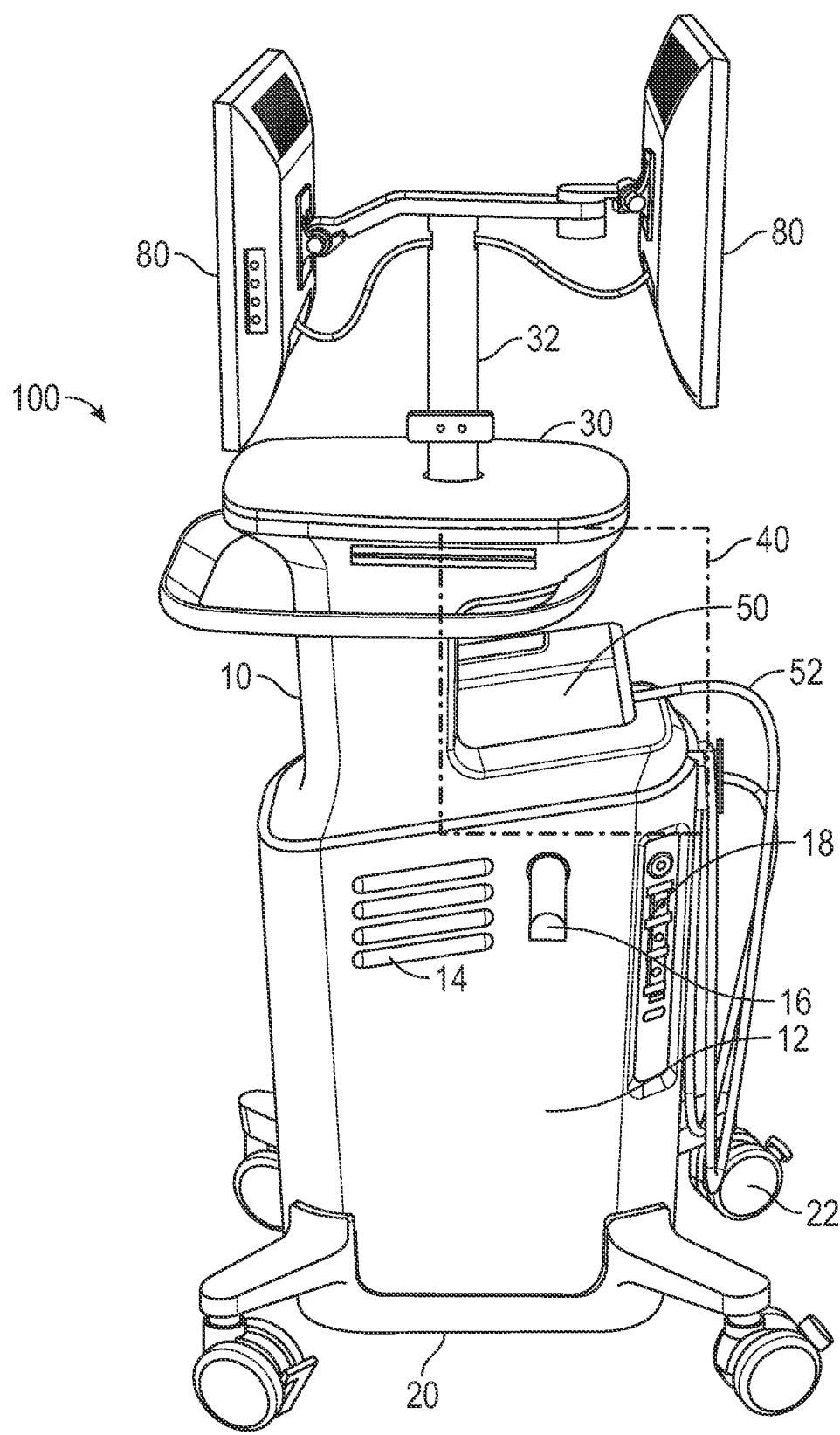
Figure 3:
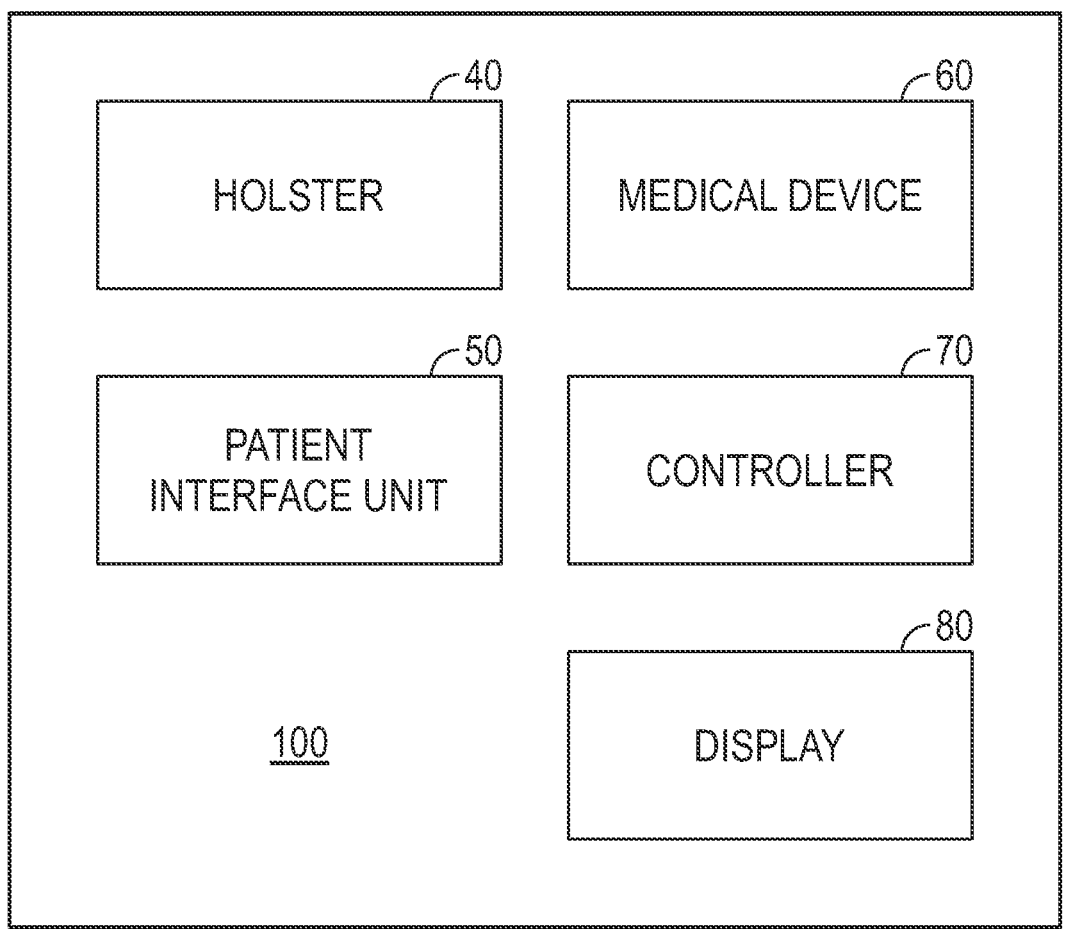
FIG. 3 is a block diagram of a medical cart apparatus according to one or more aspects of the present disclosure.
Figure 4:
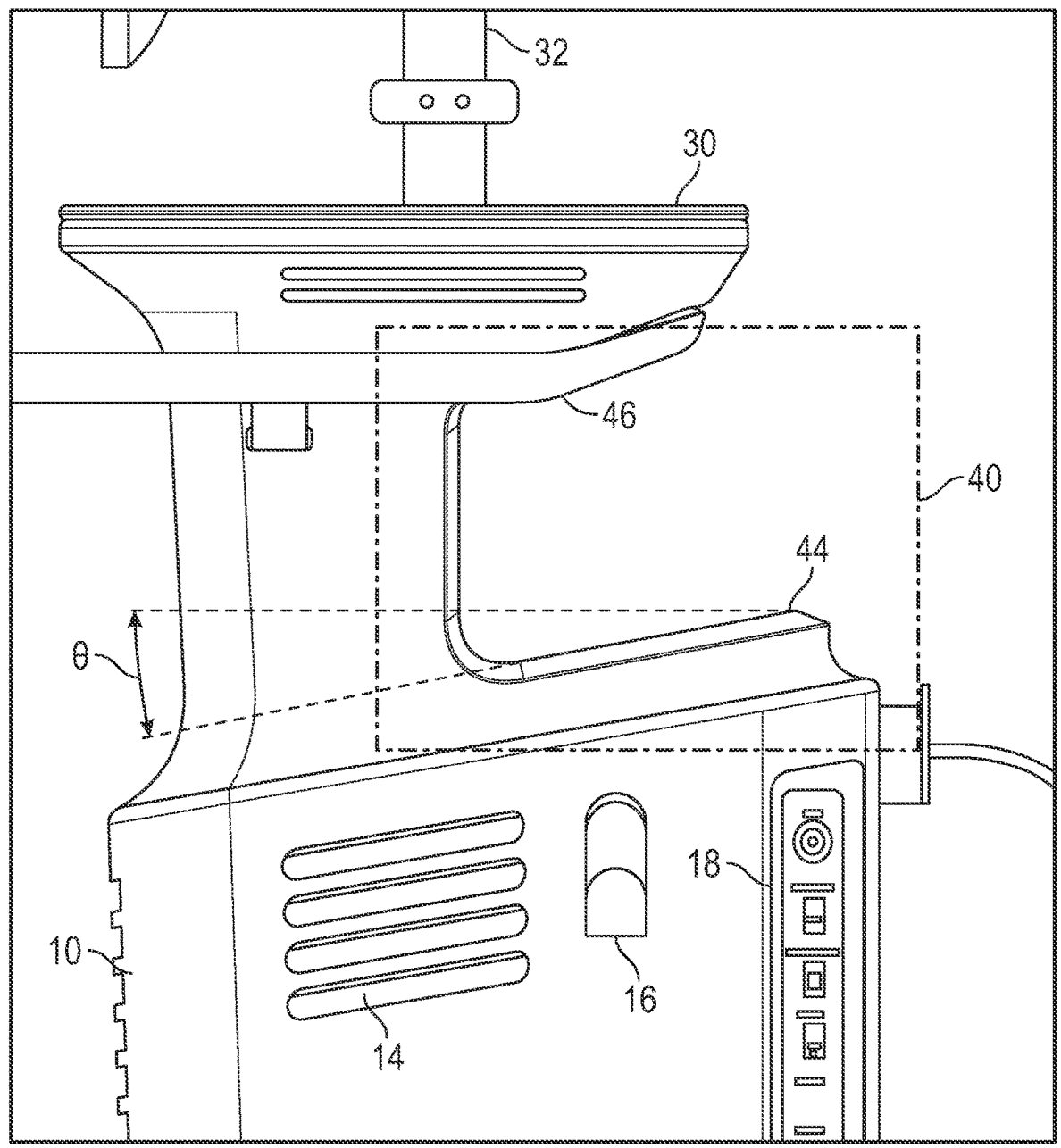
FIGS. 4-10 are various front, side, and top perspective views of a medical cart apparatus according to one or more aspects of the present disclosure.

FIGS. 1 and 2 show left side perspective views of a medical cart apparatus 100 of a first embodiment according to one or more aspects of the present disclosure. FIG. 3 shows a hardware configuration of the medical cart 100. The medical cart 100 is described below to accommodate exemplary catheterization procedures, and can be arranged to accommodate other procedures as desired.

The medical cart 100 is a mobile, portable or movable elongated body, housing or containment device. The cart 100 includes at least one or more of a holster 40, a patient interface unit (PIU) 50 or motor control unit, a medical device 60, a controller 70, and a display 80.

The cart 100 has a housing 10, a base 20 and an upper platform 30. The housing 10 has one or more sides and one or more internal storage areas or compartments to store medical items including medicine, needles, instruments, products, test equipment, or the like. The storage areas can include doors or openings that may be secured or non-secured with locks or the like. A door panel 12, for example, can be opened and closed by hinges to provide access to an internal compartment. Air vents 14 provide airflow in and out of the compartment for cooling, and can be configured to enhance the aesthetics of the cart 100.

The cart 100 has a cable hook 16 or U-shape on a side of the housing 10 under the holster 40. The cable hook 16 can be used to hang or support extraneous items such as cables, to pull the cart 100 around, or the like. The support 16 is illustrated in hook or U-shape form but can be configured in another manner. The cart 100 includes a panel 18 that can be configured with buttons, keys, LEDs (light emitting diodes), indicators, input devices, or the like, such as a power or ON-OFF switch, to indicate operational status of elements of the cart 100. The cart 100 includes a power cable located on the housing 10 to connect to a power source to provide power to software and electronics on the cart 100. The housing 10 can be configured with other elements to provide additional functions.

The base 20 supports the housing 10 through mounting members, devices, arrangements, or the like, and can include one or more wheels 22 or rollers rotatably attached to the base 20. The wheels 22 can rotate or pivot to move the cart 100 around from place to place in any direction on the floor, ground, surface, or the like, and can be configured to recess into and out of the mounting members. The wheels 22 can be configured as caster wheels or other types of wheels as desired, may be lockable or non-lockable, and may be driven or powered by a power drive.

The upper platform 30 or surface of the cart 100 is configured to adaptively hold additional elements. A mounting post 32, for example, can extend from the upper platform 30 and is configured to adaptively hold one or more displays 80 or monitors. Each display 80 can be configured to include a touch screen to enable a user to interact with the display 80 by touching or pointing at display areas on a screen to provide input, information, make selections, or the like. The display 80 is communicatively interconnected with the controller 70 in a wired or wireless manner, and can have various configurations including, for example, LCD (liquid crystal display), CRT (cathode ray tubes), LED (light emitting diode), OLED (organic LED), or another type of display.

FIGS. 4-10 show various front, side, and top perspective views of the holster 40 in more detail. The holster generally corresponds to an area associated with reference 40 throughout the drawings. The holster 40 is attached to or integrally formed together with the housing 10 at an inclined angle θ. The holster 40 is configured to ergonomically and securely store or hold items or components including, for example, the PIU 50, the medical device 60, the controller 70, or other components that can be stored in the holster 40 when not in use. The rectangular area associated with the reference 40 of the holster is for illustration purposes.

The holster 40 forms a cave or cavern and is configured as a storage area, holder, or receptacle to hold or store one or more components. The holster 40 has a back wall 41, at least one side wall 42, at least one side cut-out 43, a lip 44 or edge at an entrance of the holster 40, and a bottom surface 45 that is tilted at the angle θ with respect to a horizontal plane. The back wall 41 of the holster 40 provides a resting position of a component placed in the holster, for example a catheter. The side walls 42 provide containment for items contained in the holster 40. Side cut-outs 43 of the holster 40 provide improved visibility by allowing users to determine whether components are in the holster 40, and provide improved accessibility by allowing easy insertion and easy removal or takeout of components from the holster 40. Dimensions of an upper part of the holster 40 are configured to optimize ergonomic access of components contained therein.

As shown in FIG. 1, the holster 40 is situated at an elevation H of the cart 100 for ergonomic storing of a component and its access by hand. The angle θ can be optimized for secure positioning and mitigation of a fall-out. The side walls 42 and others around assist with protection of more sensitive medical connection areas inside. The holster 40 can be equipped with shock absorbing, dust protecting, a sealing mating gasket, or the like, on the inner wall. Also, the cave of the holster 40 can be shaped to correspond closely to the shape of components contained therein, such as the PIU 50, medical device 60, controller 70, or the like, for optimal fitting. The lip 44 adds to the security of the storage and assists with precise positioning in case of sealing of the nose section on the opposite side of a connection cable 52.

The bottom surface 45 of the holster 40 is tilted at the angle θ with a lower inner-side. The elevation H has preferably has a range between fifty-five to ninety-five centimeters (55 to 95 cm) and the angle θ is preferably within a range of five to fifty-five degrees (5 to 55°) to facilitate convenient placement and removal by hand. The holster 40 further has a lip 44 at the entrance and side cut-outs 43.

Figure 5:
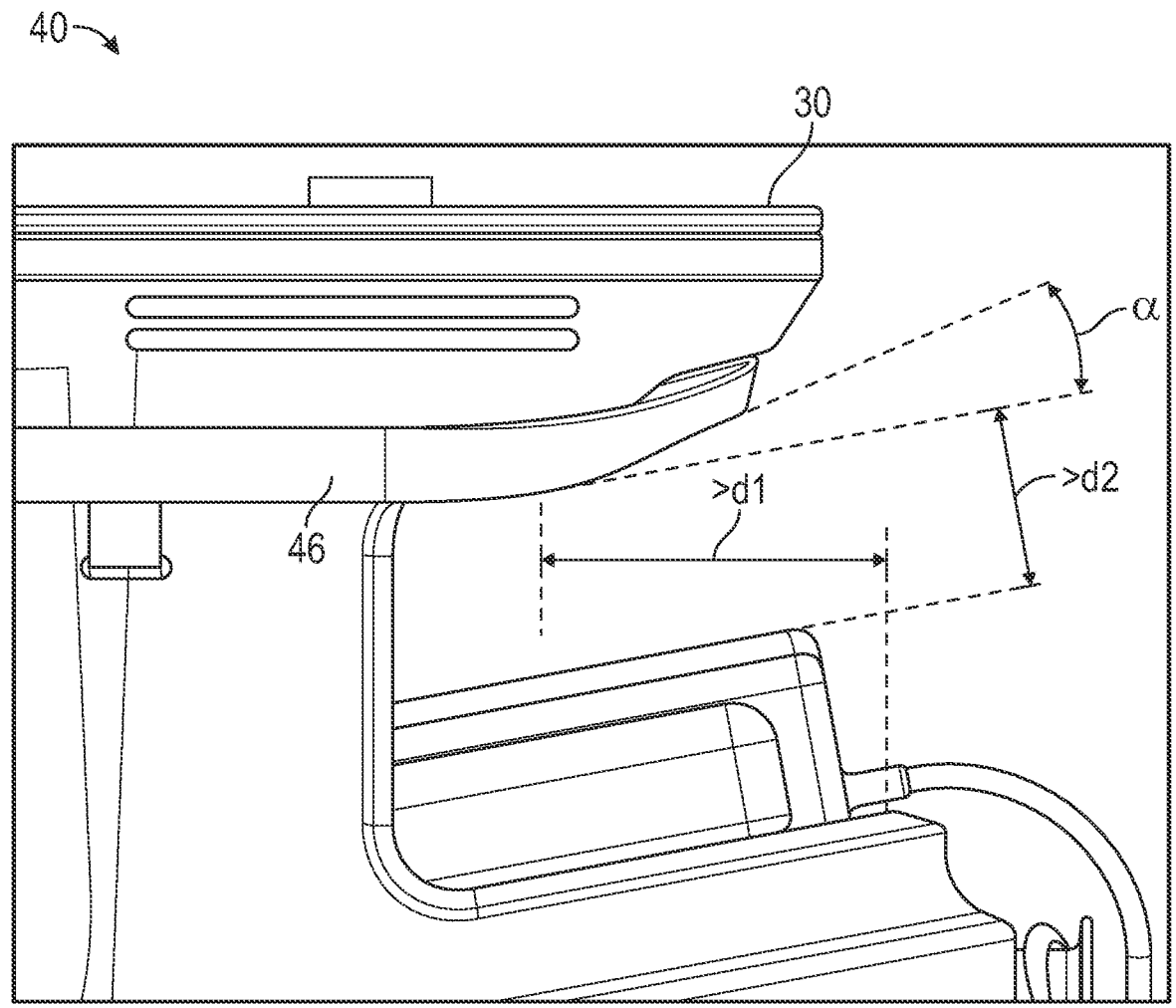
Figure 6:
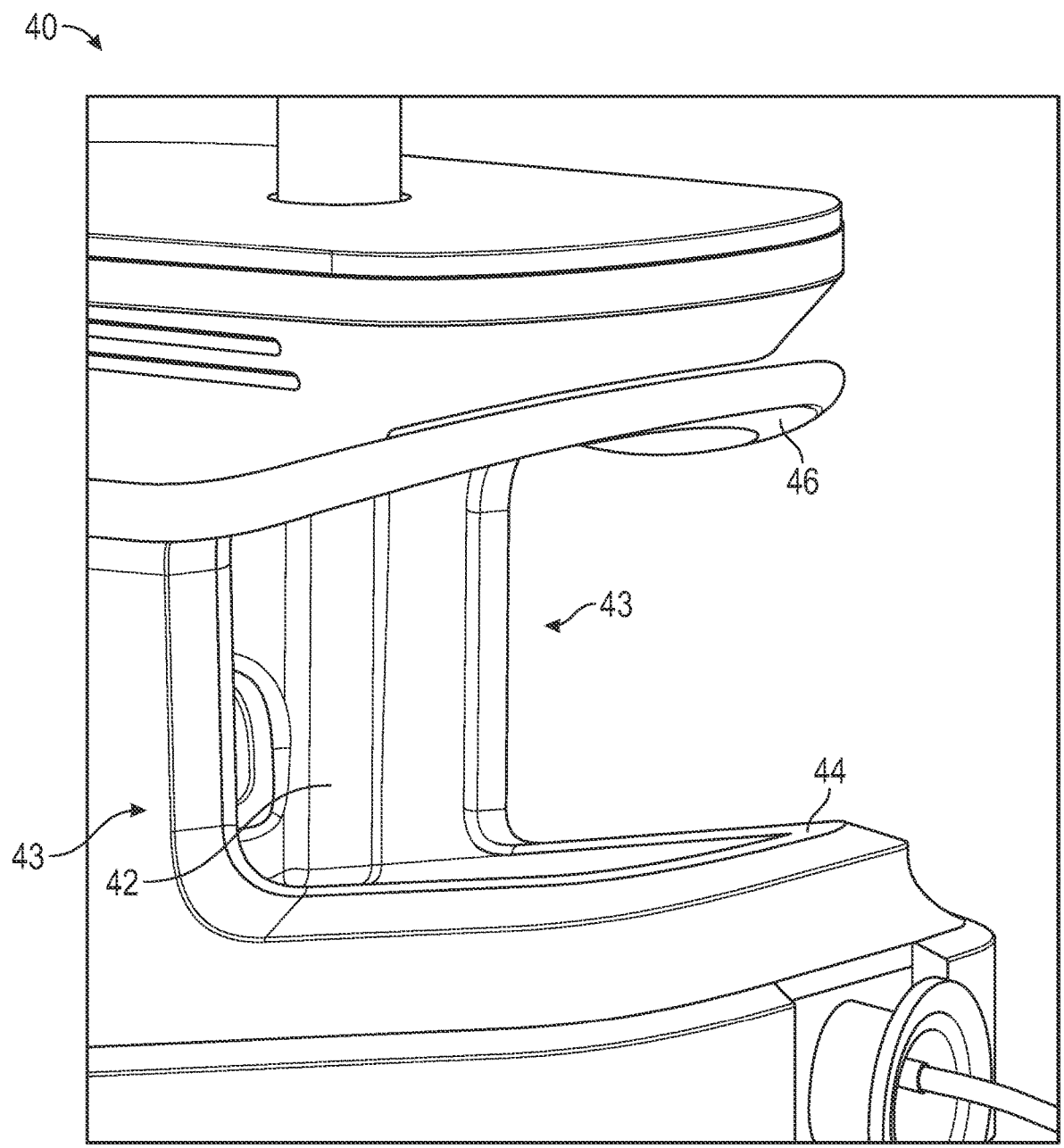
Figure 7:
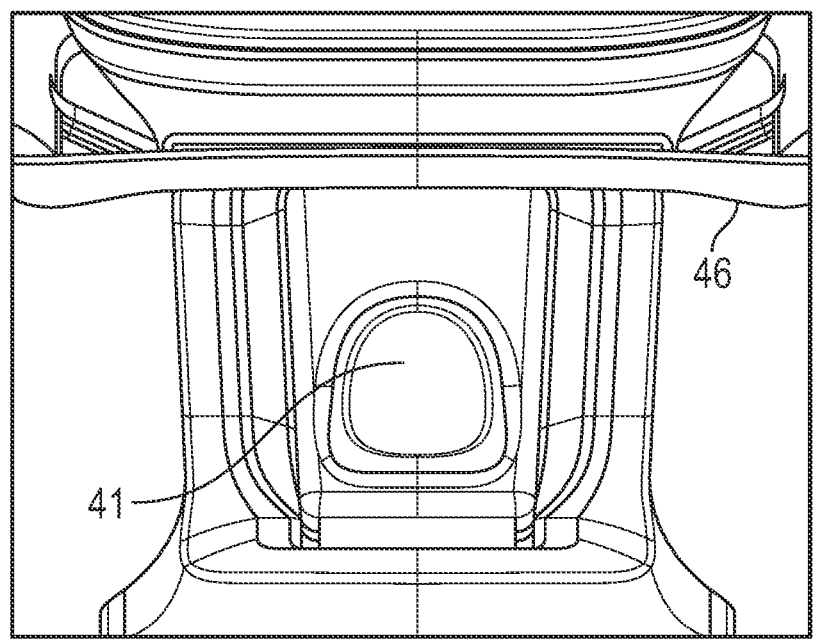
Figure 8:
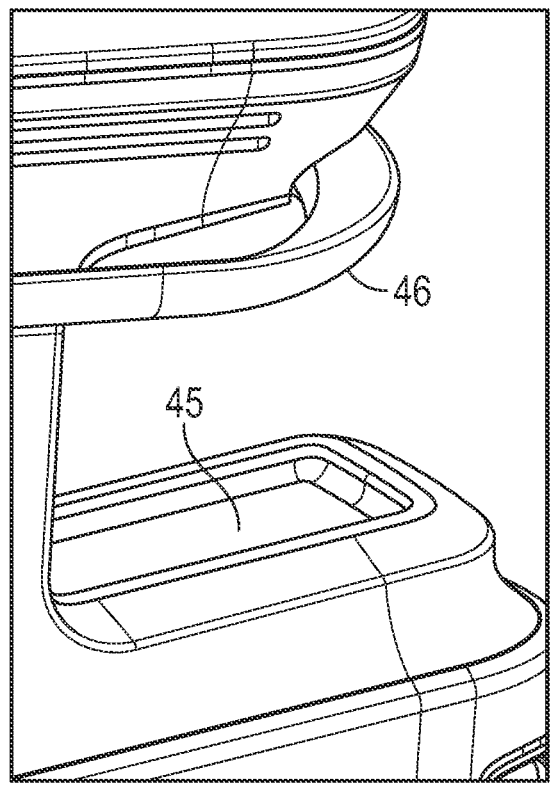
Figure 9:
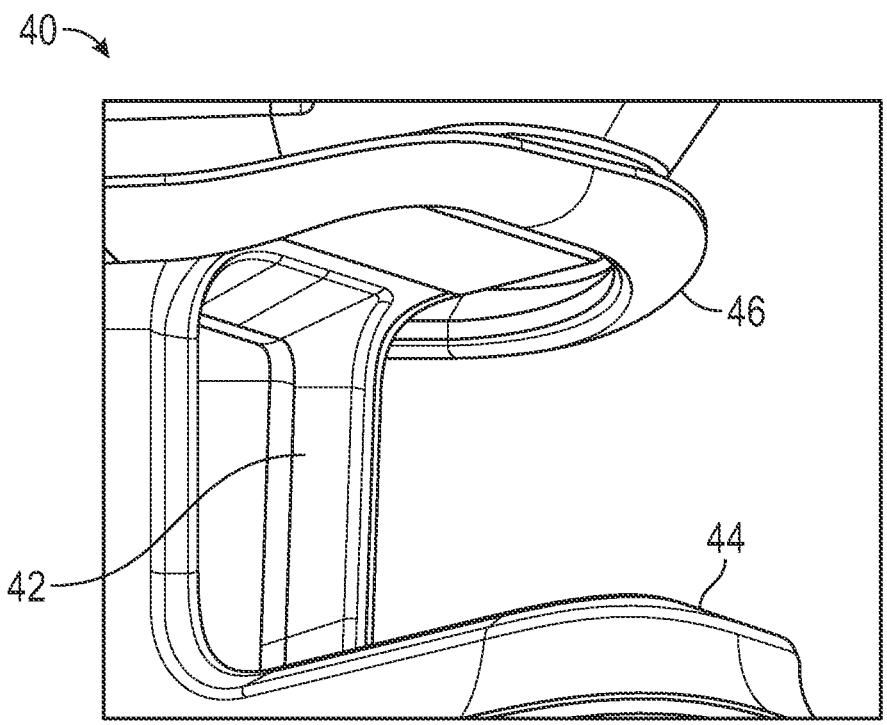
Figure 10:
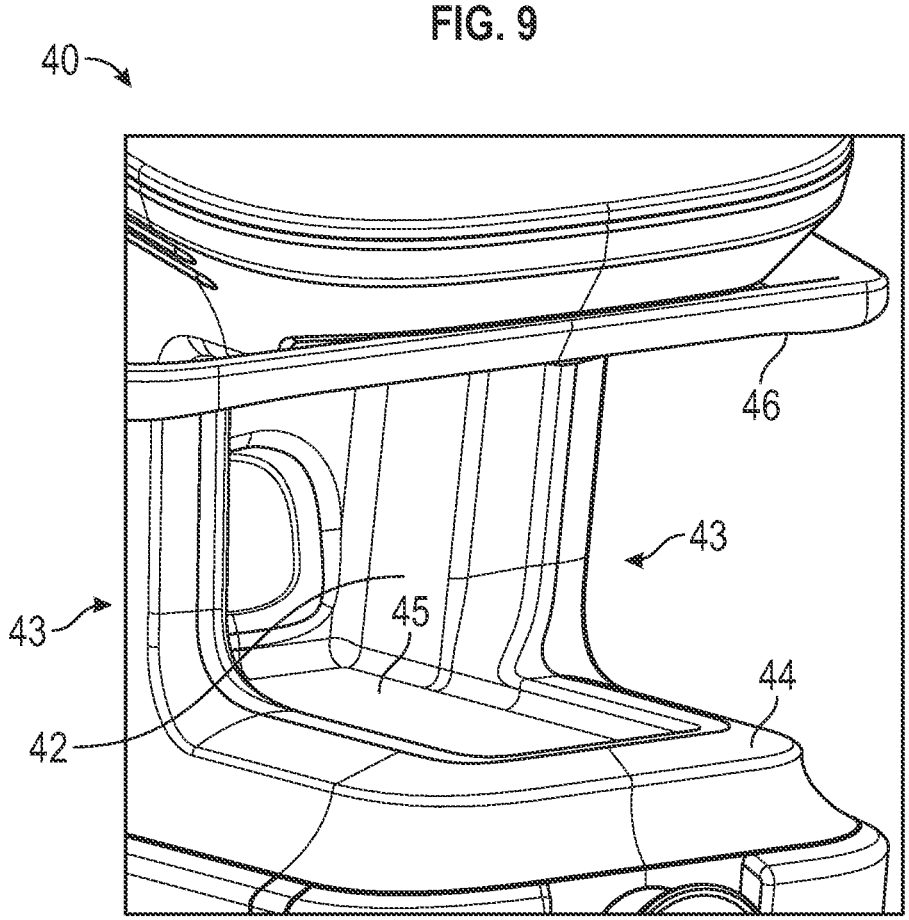

FIG. 5 shows how an upper part 46 of the holster 40 extends horizontally shorter than a base of the holster base and is optimized for ergonomic access by allowing a minimum distance d1 of 3 cm or more and allowing a hand clearance d2 of at least 2 cm or more. The upper part 46 of the holster 40 includes at least one slanting at an edge with an inclination θ+α, where α is up to 45°. The upper part 46 of the holster 40 can be used to pull the cart 100 around.

The tilt angle θ of the holster 40 provides the ability to keep components in the holster 40 when the cart is moved or bumped. The tilt angle θ ergonomically allows for removal and storage of components in the cart 100 manually or by a user's hand. The lip 44 on the holster 40 operates to keep components in the holster 40 when the cart 100 is moved or bumped. The holster 40 for the components is helpful and advantageous on the mobile cart 100 to stow the components, such as the PIU or motor control unit, when not in use.

The elevation H and the side walls 42 are optimized for ergonomic access by hand. The tilt on the holster 100 keeps any components inside the cart 100 when the cart 100 is moved or bumped.

The tilt angle θ also allows or facilitates ergonomic ease for removal and storage access of components in the cart 100 by a user's hands. The lip 44 on the holster 40 exit helps to keep components inside the cart 100 when the cart 100 is moved or bumped. The side walls 42 of the holster 40 protect the components by covering or sealing its openings as needed.

The side cut-outs 43 of the holster 100 provide improved visibility by showing whether the components are in the holster 40 or not, and provide improved accessibility by allowing easy insertion and easy takeout of the components.

The upper wall offers protection for the critical inner area and most storage volume inside the cart 100 while shaped for ergonomic access by hand ensuring convenient and secure placement and removal.

Figure 11:
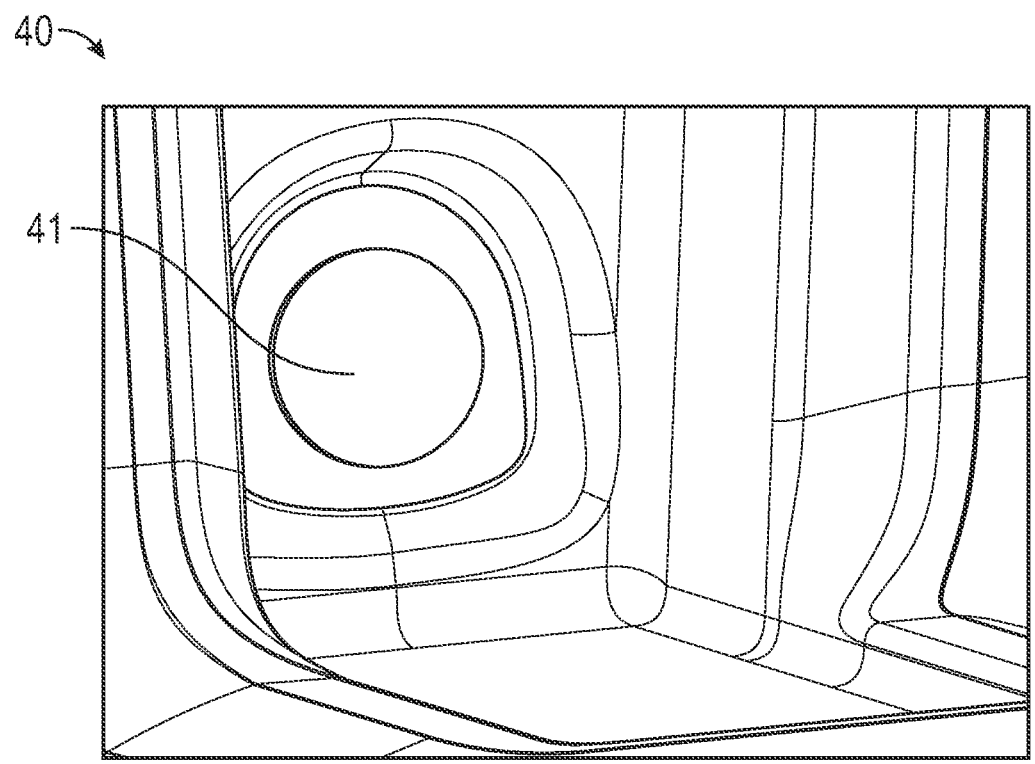
FIG. 11 is a top and front perspective views of a medical cart apparatus depicting circular padding according to one or more aspects of the present disclosure.
Figure 12:
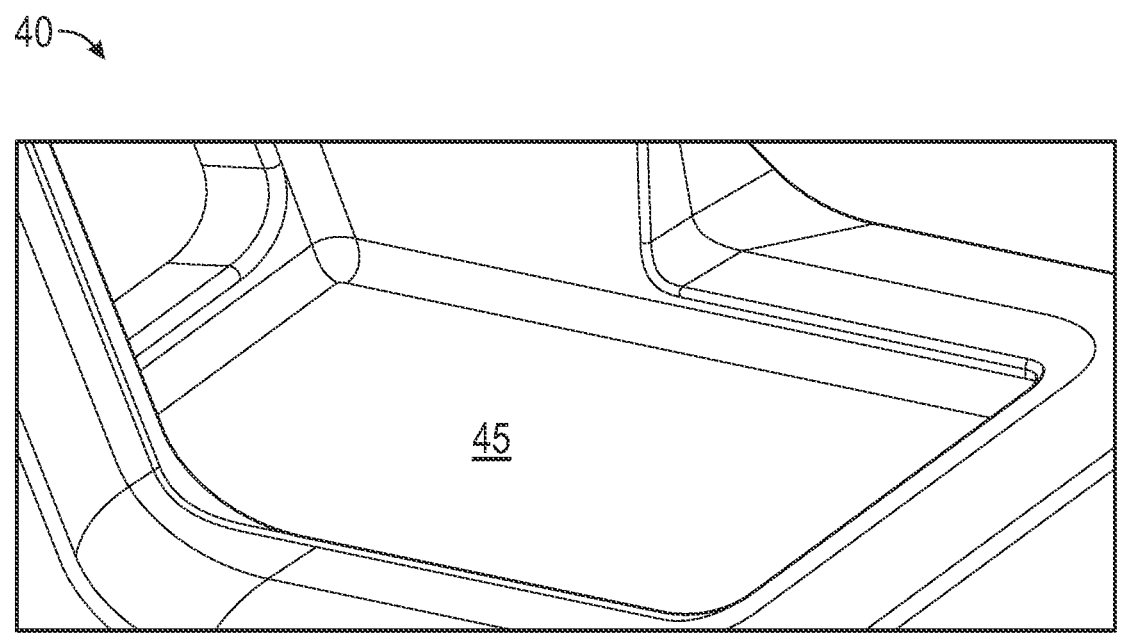
FIG. 12 is a medical cart apparatus depicting durable coating according to one or more aspects of the present disclosure.
Figure 13:
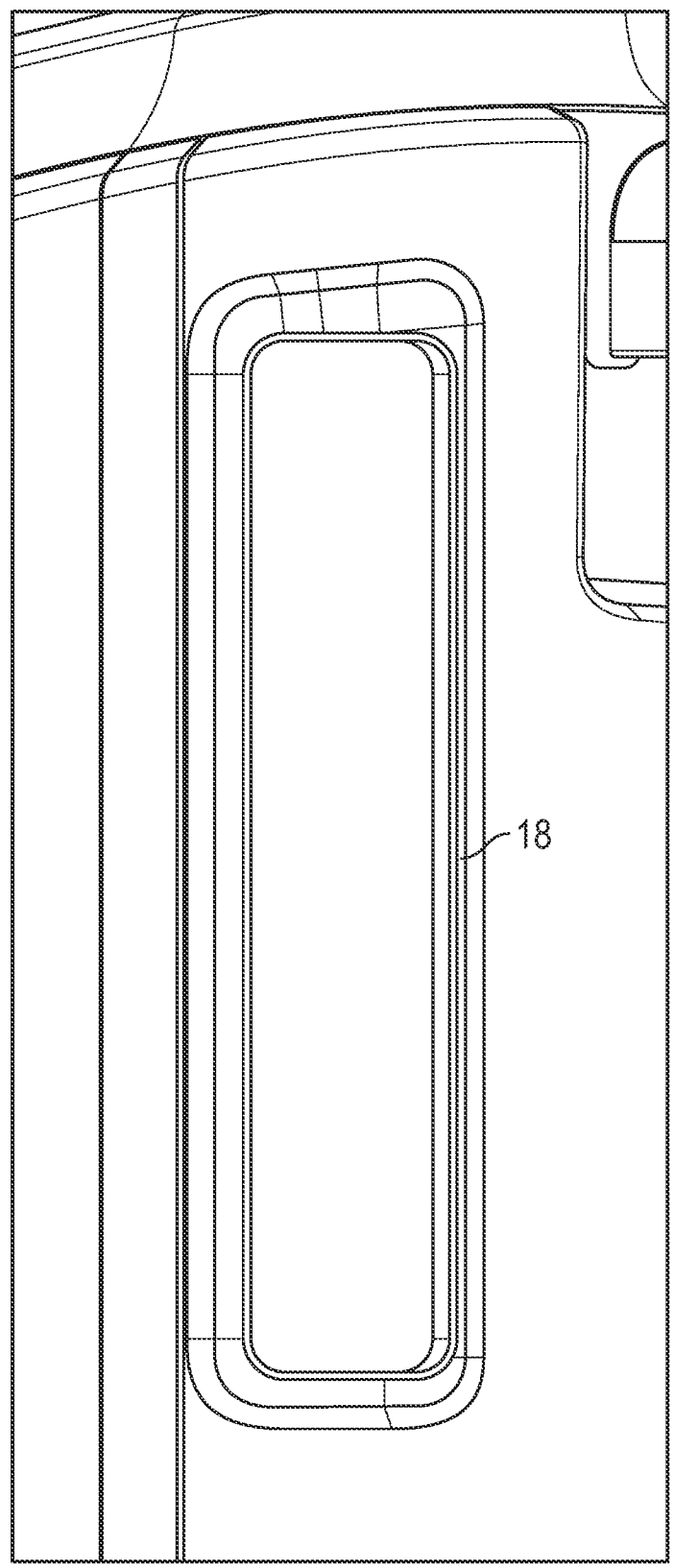
FIG. 13 is medical cart apparatus according to one or more aspects of the present disclosure.
Figure 14:
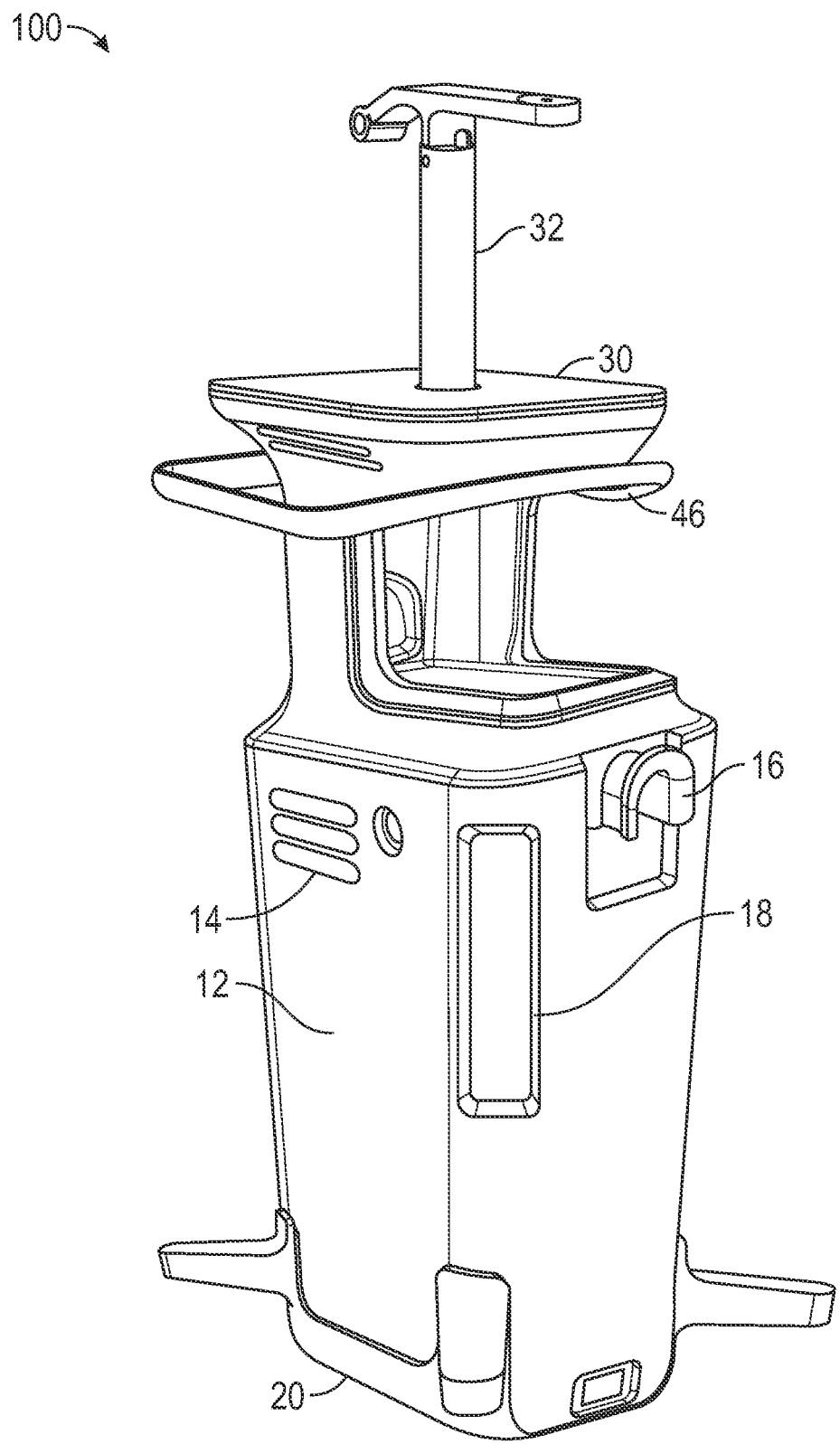
FIGS. 14-17 are top and left side perspective views of a medical cart apparatus of other embodiments according to one or more aspects of the present disclosure.
Figure 15:
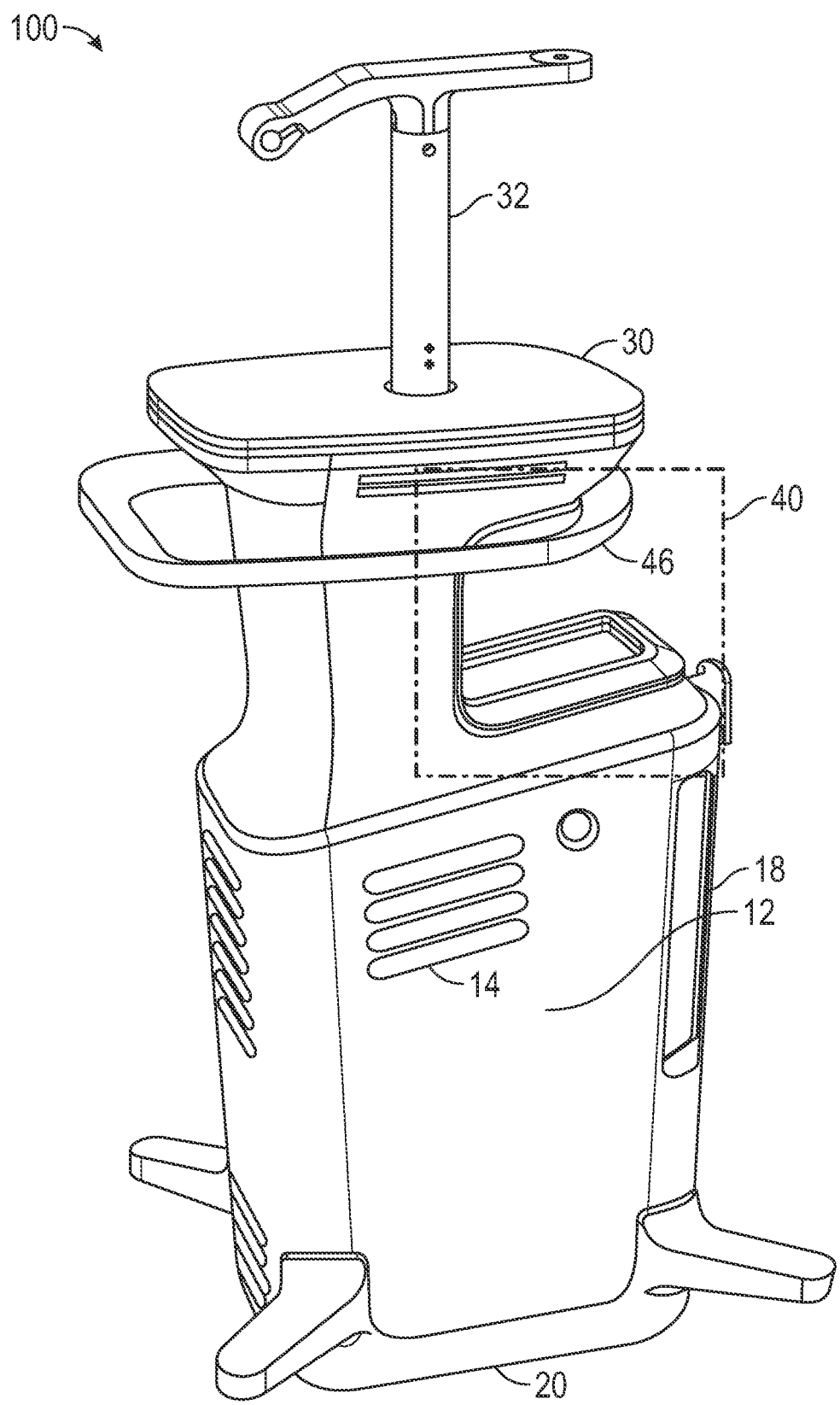
Figure 16:
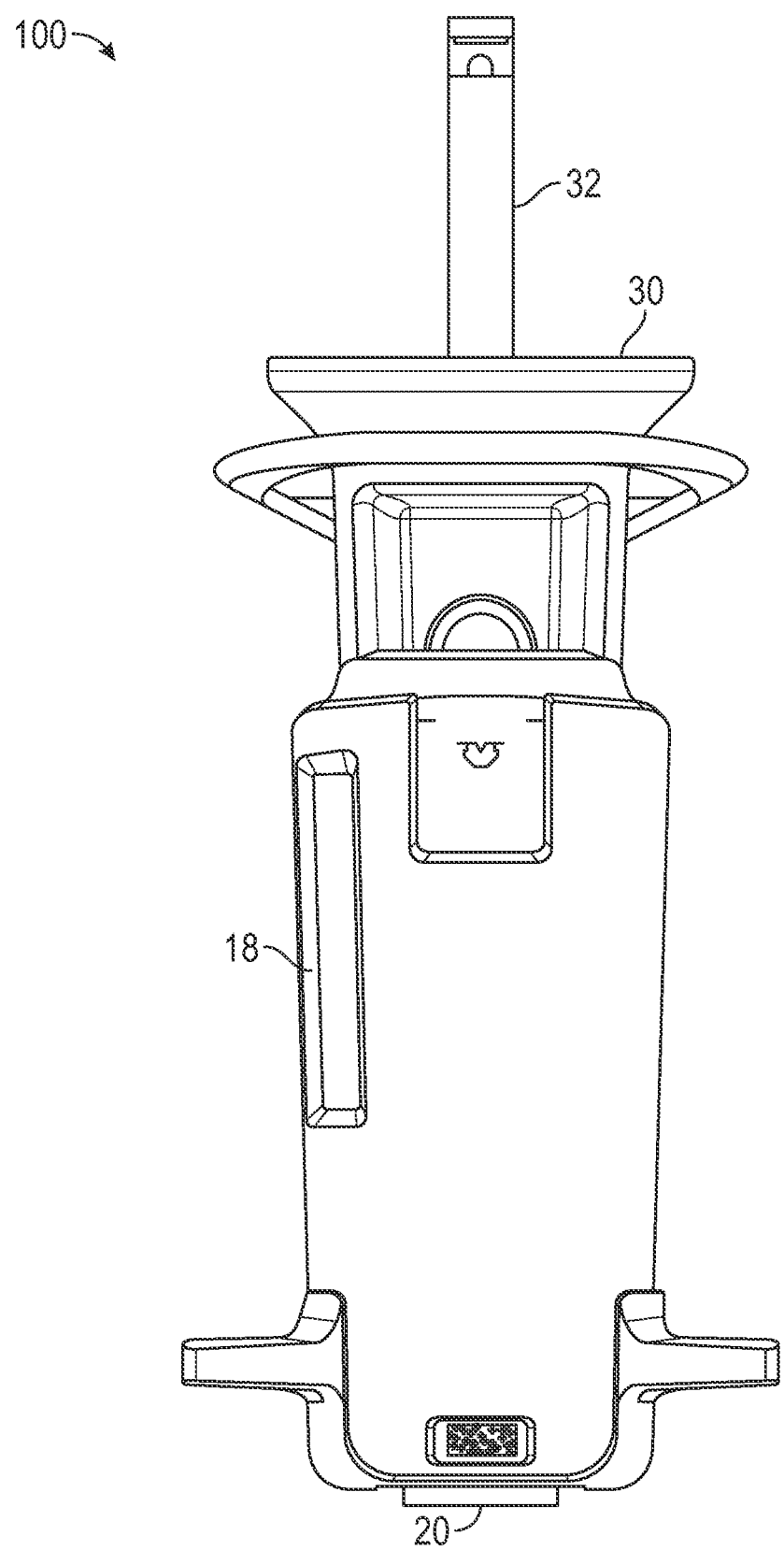
Figure 17:
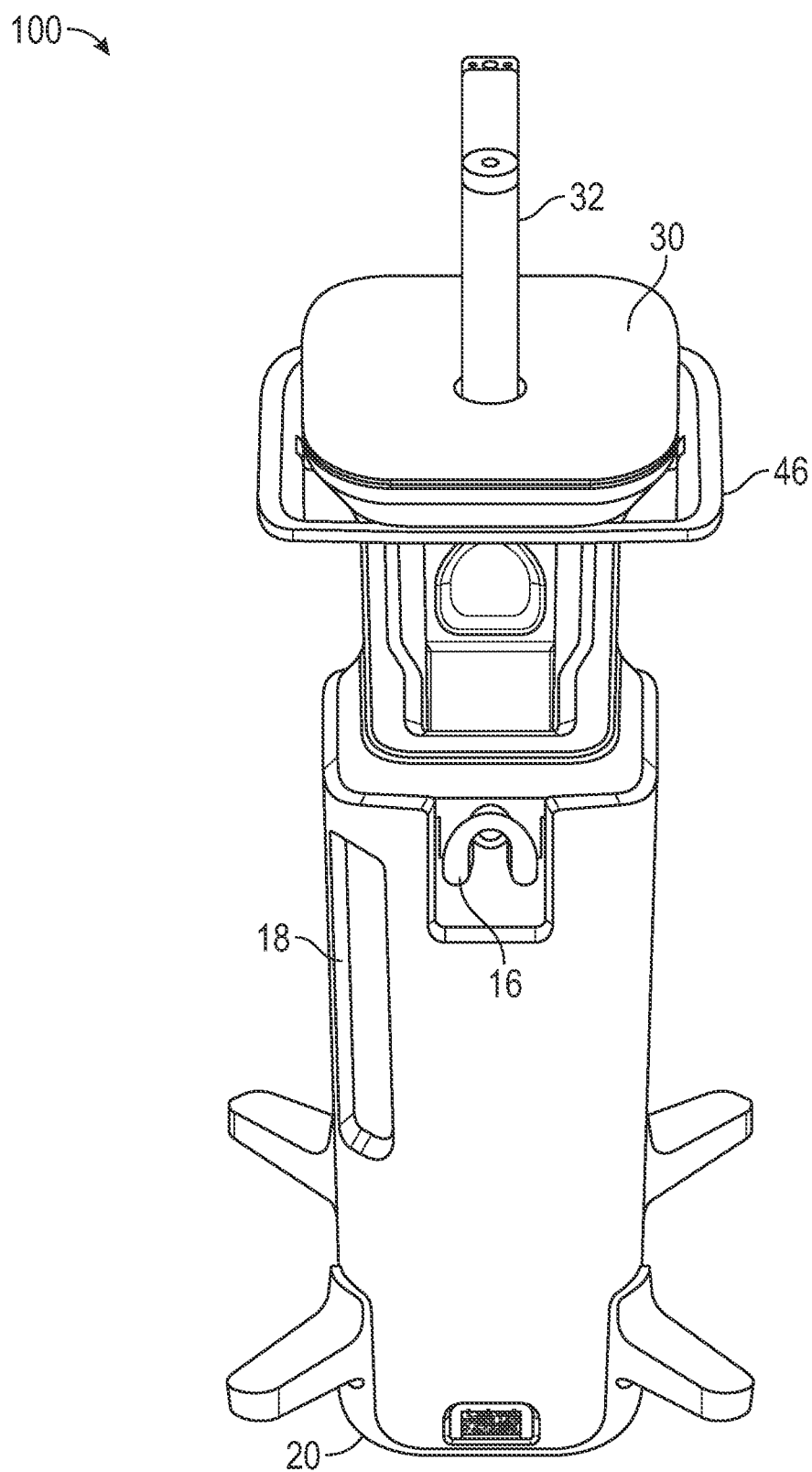

FIG. 11 depicts how the back wall 41 can have circular padding at an attachment area for a medical device 70. FIG. 12 depicts how durable coating can be provided on the bottom surface 45 of the holster 40. FIG. 13 shows the panel 18 that can be configured with buttons, keys, LEDs (light emitting diodes), indicators, input devices, or the like, such as a power or ON-OFF switch, to indicate operational status of elements of the cart 100.

The PIU 50 is a component of the cart 100 that forms an interface unit to provide patient to user interface that can be stowed or placed in the holster 40 on the cart 100. The PIU 50 is configured to be a remote unit or a motor control unit that contains optical components. As shown in FIG. 5, the holster 40 has an upper outside exposure from the top for convenient access by hand. The upper cover extends horizontally shorter than the holster 40 base by at least 3 cm or more with a hand clearance of 2 cm or more. The upper cover is configured with slanting at the edge with an inclination of θ+α where can range up to 45°.

The PIU 50 may include a probe connector and a motor which can be controlled by a processor, circuitry, or combinations thereof included in the controller 70. The controller 70 can perform image processing steps or procedures in one or more imaging modes or modalities, such as OCT (optical coherence tomography), IVUS (intravascular ultrasound), PET (positron emission tomography), SPECT (single PET), combinations thereof, or the like, and controls the information to be displayed on one or more monitors or displays. The PIU 50 includes one or more control elements to facilitate user interaction through patient input devices, such as buttons, keys, switches, or the like.

The PIU 50 can include one or more functional or voice recognition inputs such as buttons, switches, scroll wheels, cursor inputs, touch screens, microphones, pointing devices, mice, touchpads, tracking balls, styluses, cameras.

The medical device 60 can be configured as a catheter that is steerable or non-steerable and can have an elongated, flexible catheter body having proximal end and a tip section at a distal end, and at least one lumen extending therethrough. The medical device can also be configured as one or more of various other types of invasive or non-invasive arrangements including, for example, an endoscopic device, cardiovascular device, laparoscopic device, needle, stent, graft, probe, sheath, forceps, or the like. The catheter is sized and configured for insertion into a patient and can be configured as a light irradiator and a data collection probe that is disposed in the lumen of a vessel or artery, for example, and can include one or more sheaths. The catheter can include one or more of a probe tip, an optical fiber, a rotary joint, a pullback section, a connector, or the like.

The probe tip of the catheter may include one or more sensors or tracking devices, and can be threaded in the vessel or artery to collect optical, ultrasound, pressure data, or the like, and obtain images of anatomical structures within the body. The sensors may include one or more of wired or wireless accelerometers, pressure sensors, contact sensors, position sensors, mechanical stress sensors, auditory sensors, temperature sensors, or the like. The sensors provide movement or motion data that is used to determine positional movement and orientation of the medical device.

FIGS. 14-17 show one or more additional embodiments of the medical cart apparatus 100 that include at least one component, and at least one holster 40 that is tilted with respect to a horizontal plane and is configured to hold or store the component(s).

As with FIG. 1, the medical cart 100 is a mobile, portable or movable elongated body, housing or containment device. The cart 100 includes at least one or more of a holster 40, a PIU 50 or motor control unit, a medical device 60, a controller 70, and a display 80.

The cart 100 has a housing 10, a base 20 and an upper platform 30. The housing 10 has one or more sides and one or more internal storage areas or compartments to store medical items including medicine, needles, instruments, products, test equipment, or the like. The storage areas can include doors or openings that may be secured or non-secured with locks or the like. A door panel 12, for example, can be opened and closed by hinges to provide access to an internal compartment. Air vents 14 provide airflow in and out of the compartment for cooling, and can be configured to enhance the aesthetics of the cart 100.

The cart 100 has a cable hook 16 or U-shape on a side of the housing 10 under the holster 40. The cable hook 16 can be used to hang or support extraneous items such as cables, to pull the cart 100 around, or the like. The support 16 is illustrated in hook or U-shape form but can be configured in another manner. The cart 100 includes a panel 18 that can be configured with buttons, keys, LEDs (light emitting diodes), indicators, input devices, or the like, such as a power or ON-OFF switch, to indicate operational status of elements of the cart 100. The cart 100 includes a power cable located on the housing 10 to connect to a power source to provide power to software and electronics on the cart 100. The housing 10 can be configured with other elements to provide additional functions.

The base 20 supports the housing 10 through mounting members, devices, arrangements, or the like. The upper platform 30 or surface of the cart 100 is configured to adaptively hold additional elements. The mounting post 32, for example, can extend from the upper platform 30 and is configured to adaptively hold one or more elements, such as a display or monitor. The base 20 can include one or more wheels or rollers rotatably attached to the base 20. The wheels can rotate or pivot to move the cart 100 around from place to place in any direction on the floor, ground, surface, or the like, and can be configured to recess into and out of the mounting members.

The holster 40 is configured as a storage area, holder, or receptacle, and the holster has a back wall, at least one side, at least one side cut-out, a lip at an entrance of the holster, and a bottom surface that is tilted at the angle with respect to the horizontal plane. The side cut-outs of the holster provide improved visibility by showing whether a component is in the holster or not, and provide improved accessibility by facilitating or allowing easy insertion and easy takeout of the at least one component from the holster. Dimensions of the holster are configured to optimize ergonomic access of the at least one component contained therein.

The holster 40 is positioned at an elevation H, wherein a tilt of a bottom surface of the holster is an angle θ with H being within a range of 55 to 95 cm and θ being within a range of 5 to 55° to facilitate convenient placement and removal by hand. An upper cover of the holster 40 extends horizontally shorter than a base of the holster base by 3 cm or more with a hand clearance of 2 cm or more. The upper cover includes at least one slanting at an edge with an inclination θ+α, where α is up to 45°.

The medical cart 100 includes one or more of a PIU 50, a medical device 60, a controller 70, and a display 80. The medical device 60 can be a catheter. The holster 40 can include circular padding in an area to attach the at least one component, and the holster can include durable coating applied to a surface that holds the PIU 50. The PIU 50 can include a probe connector and a motor that are controlled by the controller. The PIU 50 can include optical components. The controller 60 performs image processing steps in one or more imaging modes or modalities, and controls information to be displayed on the display. The PIU can include at least one functional or voice recognition input. The controller can perform artificial intelligence or machine learning, wherein the artificial intelligence or machine learning is iterative.

As described above, a medical cart apparatus according to one or more aspects of the present disclosure includes at least one component, and at least one holster that is tilted with respect to a horizontal plane and is configured to hold or store the at least one component.

The holster is configured as a storage area, holder, or receptacle, and the holster has a back wall, at least one side, at least one side cut-out, a lip at an entrance of the holster, and a bottom surface that is tilted at the angle with respect to the horizontal plane. The side cut-outs of the holster provide improved visibility by showing whether a component is in the holster or not, and provide improved accessibility by facilitating or allowing easy insertion and easy takeout of the at least one component from the holster. Dimensions of the holster are configured to optimize ergonomic access of the at least one component contained therein.

The holster is positioned at an elevation H, wherein a tilt of a bottom surface of the holster is an angle θ with H being within a range of 55 to 95 cm and θ being within a range of 5 to 55° to facilitate convenient placement and removal by hand. An upper cover of the apparatus extends horizontally shorter than a base of the holster base by 3 cm or more with a hand clearance of 2 cm or more. The upper cover includes at least one slanting at an edge with an inclination θ+α, where α is up to 45°.

The medical cart includes one or more of a PIU 50, a medical device 60, a controller 70, and a display 80. The medical device 60 can be a catheter. The holster 40 can include circular padding in an area to attach the at least one component, and the holster can include durable coating applied to a surface that holds the PIU 50. The PIU 50 can include a probe connector and a motor that are controlled by the controller. The PIU 50 can include optical components. The controller 70 performs image processing steps in one or more imaging modes or modalities, and controls information to be displayed on the display. The display 80 can be a touch screen display. The PIU can include at least one functional or voice recognition input. The controller 70 can perform artificial intelligence or machine learning, wherein the artificial intelligence or machine learning is iterative.

The medical cart 100 can be a cart that is mobile, portable, or movable to facilitate movement of the cart on a floor or surface. The medical cart 100 has an upper section and a lower section. The upper section is attached to or integrally formed together with the lower section at an inclined angle. The holster is configured in the upper section. The lower section includes a support hook under the holster. The lower section is mounted on a base that supports the cart with one or more wheels or rollers rotatably attached to the base. The lower section has a base that supports the cart with at least one wheel or roller rotatably attached to the base. The at least one wheel or roller is lockable to lock the cart 100 in position.

Figure 18:
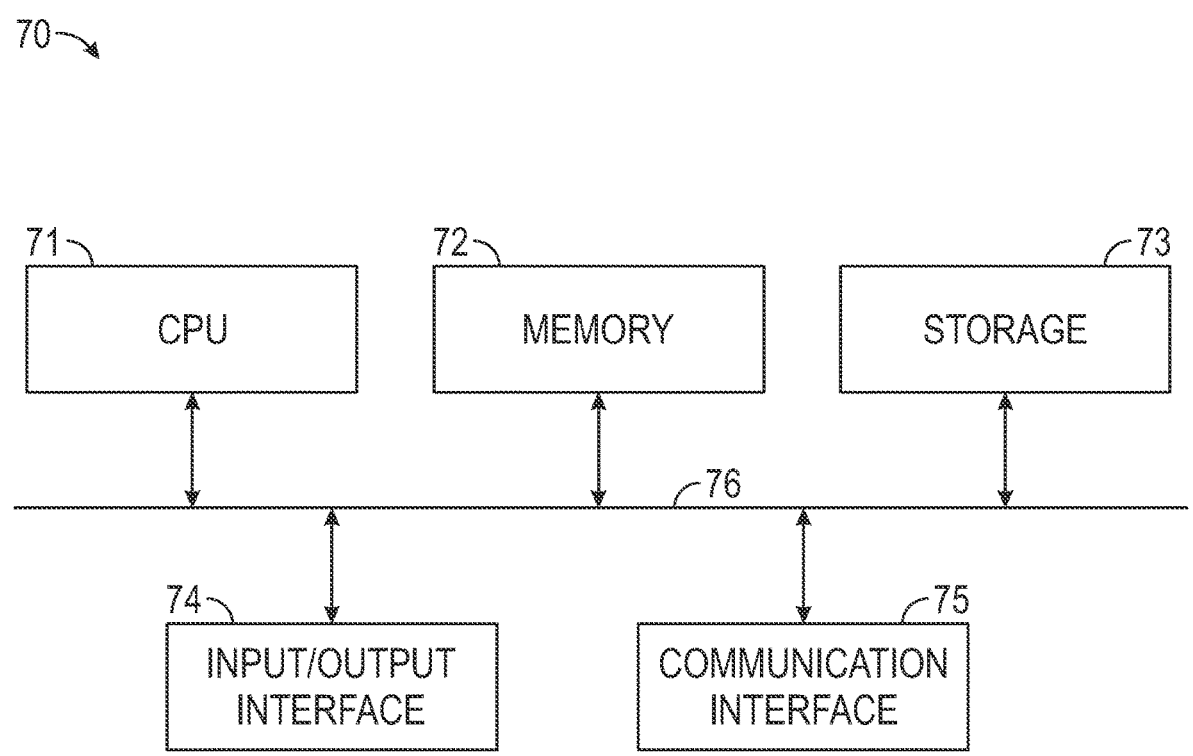
FIG. 18 is a block diagram of a controller according to one or more aspects of the present disclosure.

As shown in FIG. 18, the controller 70 has computerized configurational elements, components, modules, or the like, including one or more of a CPU 71 (central processing unit), memory 72, storage 73, input/output interface 74, communication interface 75, that are operatively interconnected by a bus 76 to perform the functions described herein. The medical cart 100 can be configured to a variety of functions where the components, process steps, data structures, or the like can be implemented using one or more operating systems computing platforms computer programs, general purpose machines, hardwired devices, FPGAs (field programmable gate arrays), ASICs (application specific integrated circuits), or the like.

The CPU 71 has one or more processors, circuitry, or a combination thereof, and retrieves instructions from memory to execute processes according to one or more aspects of the present disclosure.

The memory 72 can include ROM (read-only memory), RAM (random access memory), and external storage. ROM stores data and instructions that are implemented by the processor and other modules of the cart. The storage stores instructions and data when the cart is off or there is no power. A mass storage or removable storage can be implemented as the storage 73.

The bus 76 communicatively connects the controller 70 to input/output devices, output devices, communication devices, or other devices. The input devices are configured to enable the user to communication information and select commands to the cart configuration, and can include mouse(s), keyboards, touchscreens, or the like, with keys or buttons with alphanumeric or cursor controlled icons. The output devices are configured to display data or images generated by the cart modules, and can include printers and display devices including, for example, LCD (liquid crystal display, CRT (cathode ray tubes), LED (light emitting diode), OLED (organic LED), or the like.

The cart 100 can communicate to a network through a network adapter to be part of a computer network or a combination of networks such as the Internet (world wide web), an intranet, LAN (local area network), WAN (wide area network), or the like.

The cart 100 can be configured to include additional features including, for example, navigational positional components or tracking elements. The navigational components can manually or automatically provide positioning capabilities to the cart through use of navigation calculations using coordinates in x-y-z directions where, for example, the x-axis may be in the horizontal forward direction, the y-axis may perpendicular in the horizontal direction, and the z-axis may be in the vertical direction. The tracking elements can include one or more sensors to facilitate tracking the cart 100.

As described above, a medical cart apparatus according to one or more aspects of the present disclosure includes at least one component, and at least one holster that is tilted with respect to a horizontal plane and is configured to hold or store the at least one component.

The holster is configured as a storage area, holder, or receptacle, and the holster has a back wall, at least one side, at least one side cut-out, a lip at an entrance of the holster, and a bottom surface that is tilted at the angle with respect to the horizontal plane. The side cut-outs of the holster provide improved visibility by showing whether a component is in the holster or not, and provide improved accessibility by facilitating or allowing easy insertion and easy takeout of the at least one component from the holster. Dimensions of the holster are configured to optimize ergonomic access of the at least one component contained therein.

The holster is positioned at an elevation H, wherein a tilt of a bottom surface of the holster is an angle θ with H being within a range of 55 to 95 cm and θ being within a range of 5 to 55° to facilitate convenient placement and removal by hand. An upper cover of the apparatus extends horizontally shorter than a base of the holster base by 3 cm or more with a hand clearance of 2 cm or more. The upper cover includes at least one slanting at an edge with an inclination θ+α, where α is up to 45°.

The medical cart includes one or more of a PIU, a medical device, a controller, and a display. The medical device can be a catheter. The holster can include circular padding in an area to attach the at least one component, and the holster can include durable coating applied to a surface that holds the PIU. The PIU can include a probe connector and a motor that are controlled by the controller. The PIU can include optical components. The controller performs image processing steps in one or more imaging modes or modalities, and controls information to be displayed on the display. The display can be a touch screen display. The PIU can include at least one functional or voice recognition input. The controller can perform artificial intelligence or machine learning, wherein the artificial intelligence or machine learning is iterative.

The medical cart apparatus can be a cart that is mobile, portable, or movable to facilitate movement of the cart on a floor or surface. The medical cart apparatus has a housing and the holster is attached to or integrally formed together with the housing at an inclined angle. The housing includes a support hook under the holster. A base support supports the cart with one or more wheels or rollers rotatably attached to the base support. The wheels or rollers are lockable to lock the apparatus in position.

Additional features or aspects of present disclosure can also advantageously implement one or more AI (artificial intelligence) or machine learning algorithms, processes, techniques, or the like, to accommodate various types of medical procedures, treatment, diagnostics, or another use. Such AI techniques use a neural network, a random forest algorithm, a cognitive computing system, a rules-based engine, or the like, and are trained based on a set of data to assess types of data and generate output. For example, a training algorithm can be configured to accommodate various types of medical procedures, treatment, diagnostics, or another use using one or more models or through analysis of positional movement or orientation of the medical device.

The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g. a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the positional movement or orientation of the medical cart can be used as input data and provided to the training algorithm. Initial positional movement or orientation of the medical device can be stored in a database to facilitate precision centering of the fiber core relative to the ferrule outside diameter that are generated using input mapping to the model(s) or through expert research, and machine learning can find parameters for AI processes. Initial positional movement or orientation of the medical device are used or placed into an AI process or algorithm to facilitate precision modeling to accommodate various types of medical procedures, treatment, diagnostics, or another use. The training algorithm is configured to learn physical relationships in the input data to best describe these relationships or correlations. The data sets include information based on a number of factors including, for example, the acquired images, the number of acquired images, the angle of the image, the position of the image, detailed positional movement or orientation of the medical device, or the like. The data is evaluated using a weighted evaluation where the weights are learned through a training process, through subject matter specifications, or the like. Deep learning mechanisms can augment an AI process to accommodate various types of medical procedures, treatment, diagnostics, or another use.

A storage medium storing a program may be configured to cause a computer to execute the method to accommodate various types of medical procedures, treatment, diagnostics, or another use.

Features of the present disclosure accommodate various types of medical procedures, treatment, diagnostics, or another use.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A medical cart apparatus comprising:
   a housing;
   a base configured to support the housing;
   an upper platform positioned on top of the housing;
   at least one component; and
   at least one holster positioned below the upper platform and configured to hold or store the at least one component, the at least one holster being attached to or integrally formed with the housing and having a bottom surface and an upper part each having a length,
   wherein the bottom surface is tilted at an angle θ with respect to a horizontal plane, and the length of the upper part is shorter than the length of the bottom surface.

2. The medical cart apparatus according to claim 1, wherein the holster is configured as a storage area, holder, or receptacle.

3. The medical cart apparatus according to claim 1, wherein the holster further has a back wall, at least one side wall, at least one side cut-out, and a lip at an entrance of the holster.

4. The medical cart apparatus according to claim 3, wherein the at least one side cut-out of the holster provides visibility by showing whether the at least one component is in the holster or not, and provides accessibility by facilitating or allowing easy insertion and easy takeout of the at least one component from the holster.

5. The medical cart apparatus according to claim 1, wherein dimensions of the holster are configured to optimize ergonomic access of the at least one component contained therein.

6. The medical cart apparatus according to claim 1, wherein the holster is positioned at an elevation H being within a range of 55 to 95 cm and the angle θ being within a range of 5 to 55° to facilitate convenient placement and removal by hand.

7. The medical cart apparatus according to claim 1, wherein the upper part of the apparatus extends horizontally shorter than the bottom surface of the holster base by 3 cm or more with a hand clearance of 2 cm or more.

8. The medical cart apparatus according to claim 7, wherein the upper part includes at least one slanting surface at an edge with an inclination θ+α, where α is up to 45°.

9. The medical cart apparatus according to claim 1, further comprising one or more of a controller and a display, wherein the at least one component comprises one or more of a PIU (patient interface unit) and a medical device.

10. The medical cart apparatus according to claim 9, wherein the medical device is a catheter.

11. The medical cart apparatus according to claim 9, wherein the holster includes circular padding in an area to attach the at least one component.

12. The medical cart apparatus according to claim 9, wherein the holster includes durable coating applied to a surface that holds the PIU.

13. The medical cart apparatus according to claim 9, wherein the PIU comprises a probe connector and a motor that are controlled by the controller.

14. The medical cart apparatus according to claim 9, wherein the PIU comprises optical components.

15. The medical cart apparatus according to claim 9, wherein the controller performs image processing steps in one or more imaging modes or modalities.

16. The medical cart apparatus according to claim 9, wherein the controller controls information to be displayed on the display.

17. The medical cart apparatus according to claim 9, wherein the display is a touch screen display.

18. The medical cart apparatus according to claim 9, wherein the PIU includes at least one functional or voice recognition input.

19. The medical cart apparatus according to claim 9, wherein the controller performs artificial intelligence or machine learning.

20. The medical cart apparatus according to claim 19, wherein the artificial intelligence or machine learning is iterative.

21. The medical cart apparatus according to claim 1, wherein the apparatus is a cart that is mobile, portable, or movable to facilitate movement of the cart on a floor or surface.

22. The medical cart apparatus according to claim 1, wherein the holster is attached to or integrally formed together with the housing at an inclined angle.

23. The medical cart apparatus according to claim 1, wherein the housing comprises a support hook under the holster.

24. The medical cart apparatus according to claim 1, wherein the base supports the cart with one or more wheels or rollers rotatably attached to the base.

25. The medical cart apparatus according to claim 24, wherein the one or more wheels or rollers are lockable to lock the apparatus in position.

\* \* \* \* \*